(12) United States Patent
Martz et al.

(10) Patent No.: US 12,106,587 B2
(45) Date of Patent: Oct. 1, 2024

(54) USING FI-RT TO GENERATE WINE SHOPPING AND DINING RECOMMENDATIONS

(71) Applicant: PENROSE HILL, Napa, CA (US)

(72) Inventors: Matthew K. Martz, Chapel Hill, NC (US); Philip James, New York, NY (US); Erik Steigler, New York, NY (US)

(73) Assignee: PENROSE HILL, Napa, CA (US)

(*) Notice: Subject to any disclaimer, the term of this patent is extended or adjusted under 35 U.S.C. 154(b) by 377 days.

(21) Appl. No.: 17/589,244

(22) Filed: Jan. 31, 2022

(65) Prior Publication Data

US 2023/0245475 A1    Aug. 3, 2023

(51) Int. Cl.

| | |
|---|---|
| *G06V 20/62* | (2022.01) |
| *G01N 21/3577* | (2014.01) |
| *G01N 33/14* | (2006.01) |
| *G06K 19/06* | (2006.01) |
| *G06K 19/07* | (2006.01) |
| *G06V 10/764* | (2022.01) |
| *G06V 30/10* | (2022.01) |

(52) U.S. Cl.
CPC ......... *G06V 20/62* (2022.01); *G01N 21/3577* (2013.01); *G01N 33/146* (2013.01); *G06K 19/06028* (2013.01); *G06K 19/06037* (2013.01); *G06K 19/0723* (2013.01); *G06V 10/764* (2022.01); *G06V 30/10* (2022.01)

(58) Field of Classification Search
CPC ...... G06V 20/62; G06V 10/764; G06V 30/10; G06V 10/143; G06V 10/82; G06V 20/68; G01N 21/3577; G01N 33/146; G01N 2201/1296; G01N 2021/3595; G06K 19/06028; G06K 19/06037; G06K 19/0723
USPC ......................................................... 382/103
See application file for complete search history.

(56) References Cited

U.S. PATENT DOCUMENTS

| | | | | |
|---|---|---|---|---|
| 2010/0222224 | A1* | 9/2010 | Suni .................... | G01N 33/5438 506/8 |
| 2018/0136185 | A1* | 5/2018 | Agostinelli .......... | G01N 27/023 |
| 2018/0168385 | A1* | 6/2018 | Boone ................. | G06Q 30/0621 |
| 2021/0215657 | A1* | 7/2021 | Rippee ................ | G06Q 30/0201 |

FOREIGN PATENT DOCUMENTS

| | | | | |
|---|---|---|---|---|
| CA | 2783493 | * | 1/2013 | |
| CN | 109060712 | * | 12/2018 | ......... G01N 21/3577 |
| DE | 19638548 | * | 3/1998 | ............. G06Q 30/02 |

* cited by examiner

*Primary Examiner* — Jerome Grant, II
(74) *Attorney, Agent, or Firm* — Buckley, Maschoff & Talwalkar LLC

(57) ABSTRACT

Some embodiments of the present disclosure relate to systems and methods including acquiring an image including an indication of at least one wine; identifying, by optical character recognition, the at least one wine in the acquired image; correlating each of the identified at least one wines to a visual image representation of each wine; and executing a trained computer vision classification system using the visual image representation of each of the identified wines and labeled visual image representations of at least one wine associated with a user flavor profile including at least one classification as inputs to generate an output including, for each of the identified wines, an indication of whether the identified wine corresponds to the at least one classification associated with the user flavor profile.

17 Claims, 8 Drawing Sheets

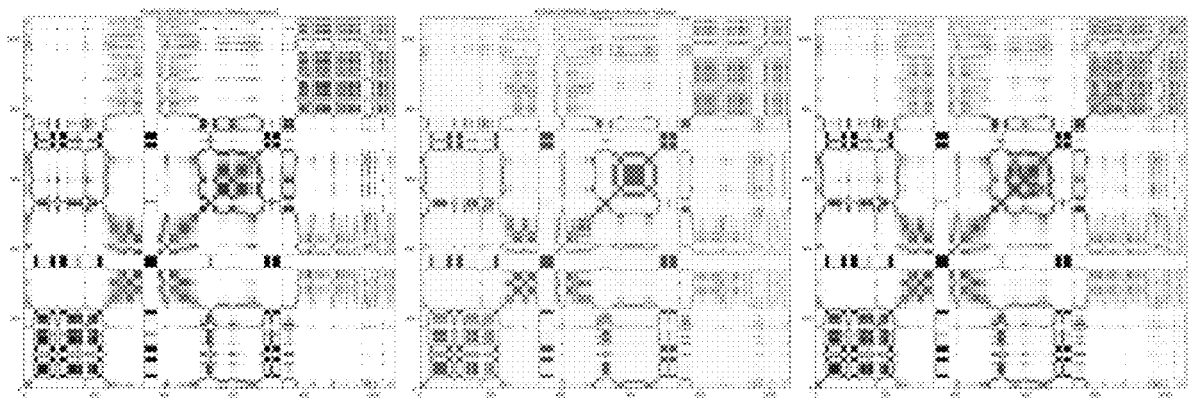
*FIG. 2A*  *FIG. 2B*  *FIG. 2C*

500

505 — IDENTIFY, BY OPTICAL CHARACTER RECOGNITION, THE AT LEAST ONE WINE IN THE ACQUIRED IMAGE

510 — CORRELATE EACH OF THE IDENTIFIED AT LEAST ONE WINES TO A VISUAL IMAGE REPRESENTATION OF EACH WINE

515 — EXECUTE A TRAINED COMPUTER VISION CLASSIFICATION SYSTEM USING (1) THE VISUAL IMAGE REPRESENTATION OF EACH OF THE IDENTIFIED WINES AND (2) LABELED VISUAL IMAGE REPRESENTATIONS OF AT LEAST ONE WINE ASSOCIATED WITH A USER FLAVOR PROFILE INCLUDING AT LEAST ONE CLASSIFICATION AS INPUTS TO GENERATE AN OUTPUT INCLUDING, FOR EACH OF THE IDENTIFIED WINES, AN INDICATION OF WHETHER THE IDENTIFIED WINE CORRESPONDS TO THE AT LEAST ONE CLASSIFICATION ASSOCIATED WITH THE USER FLAVOR PROFILE

*FIG. 5*

USING FI-RT TO GENERATE WINE SHOPPING AND DINING RECOMMENDATIONS

BACKGROUND

Conventionally, consumable items such as food and beverages, including wine for example, might be produced using well-established techniques and procedures. An expert knowledgeable of the items being produced might classify the quality of the produced items based on the expert's stated taste, smell, and feel of the items. Such evaluations of the produced items might be useful in determining, for example, the quality of the items, pricing for the items, suitable uses/markets for the items, compliance of the items with applicable regulatory and/or industry policies, etc. However, such evaluations are inextricably limited by the experience, availability, and personal preferences/biases of the "experts".

Some systems and processes have been developed to evaluate food and beverages using, at least in part, machine-based systems that might detect and/or categorize food and beverage samples based on calibrated measurements (e.g., chemical properties, etc.) provided using one or more different technologies. Some of the technologies used include, for example, mass spectrometry, gas chromatography, and other analytical tools and processes. A feature of at least some of these systems is that the machines and systems are calibrated to detect a particular chemical compound, where the particular chemical compound has one or more characteristic features that can be detected and identified by the calibrated system. However, a limitation of such systems is that the machine or system is calibrated to look for specific, known chemical compounds (e.g., percentage of alcohol in a wine sample).

Determining, by chemical analysis, one or more characteristic features of a wine or other consumable item during the various stages of producing those items may benefit, for example, improvements in and/or compliance to desired production processes. However, such chemical analysis has not traditionally been readily or efficiently used by consumers of such consumable items.

Accordingly, it would therefore be desirable to provide a system and method to detect and recognize consumable items and provide recommendations related thereto, in an efficient and data-driven manner.

BRIEF DESCRIPTION OF THE DRAWINGS

FIGS. 2A-2C are illustrative example depictions of a visual images derived from a conversion of the wave spectra graphs in FIGS. 1A-1C, respectively;

FIG. 5 is an illustrative flow diagram for a process, according to some embodiments;

Figures 1A, 1B, 1C:
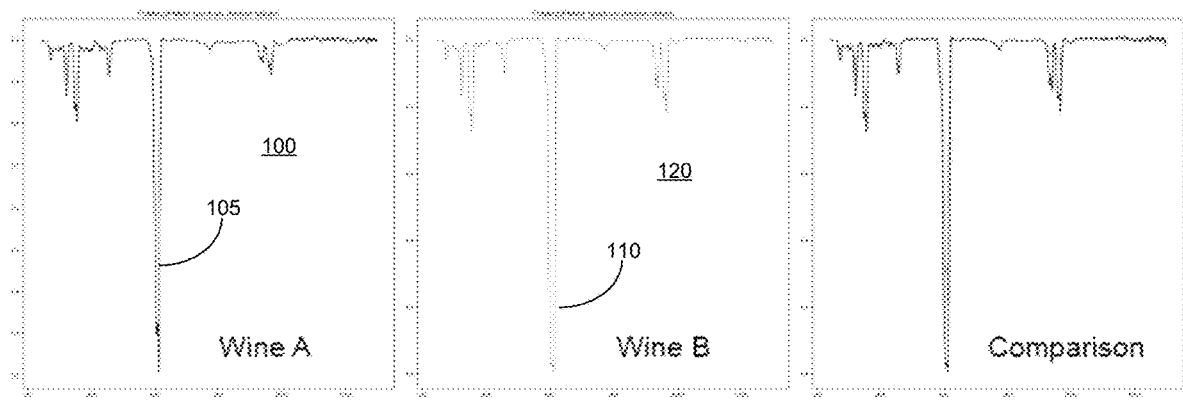
FIGS. 1A-1C are illustrative depictions of wave spectra graphs for wine samples.

Throughout the drawings and the detailed description, unless otherwise described, the same drawing reference numerals will be understood to refer to the same elements, features, and structures. The relative size and depiction of these elements may be exaggerated or adjusted for clarity, illustration, and/or convenience.

DETAILED DESCRIPTION

In the following detailed description, numerous specific details are set forth in order to provide a thorough understanding of embodiments. However, it will be understood by those of ordinary skill in the art that the embodiments may be practiced without these specific details. In other instances, well-known methods, procedures, components and circuits have not been described in detail so as not to obscure the embodiments.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are system, method and/or computer program product embodiments, and/or combinations and sub-combinations thereof, to provide and support building (i.e., generating) a computer vision classification model or system that is trained using visual image representations (also referred to herein at various times simply as an images) derived or converted from raw spectroscopy data of an analyzed sample (e.g., a wine sample analyzed by infrared spectroscopy). In some embodiments, aspects of transfer learning might be applied to a pre-trained computer vision model, system, or algorithm to facilitate efficient training of the computer vision classification model or system using the image(s) of the wine sample. The present disclosure also provides system, method and/or computer program product embodiments, and/or combinations and sub-combinations thereof, to provide and support using a classification model or system as disclosed herein to provide a number and variety of practical applications. Some embodiments include use-cases related to, for example, a detection of environmental perturbations, determining customer cohort flavor profiles, categorizing and labeling of analyzed samples (e.g., wine samples), and other calculated, determined, and predictive outputs. Some embodiments of a classification model or system disclosed herein might use or leverage a pre-trained computer vision model, system, or algorithm implementing a neural network (e.g., a convolutional neural network, CNN) for computer vision that is pre-trained to perform one or more computer vision tasks (e.g., vision recognition, segmentation, classification, etc.).

FIGS. 1A-1C are illustrative depictions of example wave spectra graphs for wine samples analyzed by infrared spectroscopy, in accordance with some embodiments herein. As used herein, infrared spectroscopy generally refers to the measurement of the interaction of radiation in the infrared region of the electromagnetic spectrum with a sample of matter by absorption, emission, or reflection, based on the fact that molecules absorb frequencies that are characteristic of their structure. Infrared spectroscopy encompasses a range of measurement techniques. In some embodiments herein, Fourier-transform Infrared Spectroscopy (Fi-RT) might be the type of infrared spectroscopy measurement technique used to record infrared spectra where the Fourier transform is performed on the raw infrared spectroscopy data to obtain an output representing light output as a function of infrared wavelength (or its equivalent wave number). FIGS 1A-1C are examples of infrared wave spectra graphs obtained using Fi-RT. The peaks in the wave spectra in FIGS. 1A-1C correspond to the region(s) where specific compound(s) the infrared spectroscopy machine is calibrated to detect are absorbing and exciting at a particular wavelength and its measured relative value. For example, the infrared spectroscopy machine might be calibrated to detect alcohol in a wine sample and the largest peak in FIGS. 1A and 1B (peak 105 and peak 110, respectively) might indicate the particular wavelength alcohol absorption is detected and its measured relative value.

As an example, FIG. 1A is an illustrative depiction of a wave spectra graph of a first wine sample (e.g., wine A) analyzed by Fi-RT, FIG. 1B is an illustrative depiction of a wave spectra graph of a second wine sample (e.g., wine B) analyzed by Fi-RT, and FIG. 1C is an illustrative depiction of a combined wave spectra graph where the wave spectra of the first wine sample and the second wine sample are depicted on the same graph. In some regions of the combined wave spectra graph of FIG. 1C, a portion of the wave spectra of the first wine sample and the wave spectra of the second wine sample have the same representative value(s), with one wave spectra being overlaid the other wave spectra. In other regions of the combined wave spectra graph of FIG. 1C, the wave spectra of the first wine sample and the wave spectra of the second wine sample are not consistent with each other. That is, FIG. 1C might provide or facilitate a comparison of the similarities and differences between the wave spectra of wine A and the wave spectra of wine B for detected chemical compounds.

As demonstrated by FIGS. 1A-1C, wave spectra might be used to effectively identify particular chemical compounds as represented by measurements at specific wavelengths (i.e., peaks). In some aspects, it may be desirable to use the full extent of the spectra data to, for example, classify, evaluate, compare, and other processes, of analyzed (wine) samples. For example, instead of comparing analyzed samples at particular wavelengths by machines designed to measure calibrated portions of the (infrared) spectrum, it may be beneficial to view and compare a full extent of the spectra for the (wine) samples. Use of the full spectra data might facilitate and support, for example, the detection (i.e., identifying) of unknown or unidentified chemical compounds, and chemical compounds not yet identified as being in a particular type of sample. For example, a technique that uses the full spectra of a (wine) sample might identify a chemical compound not previously identified as being present in wine or other sample being analyzed. The identification or detection of such unidentified chemical compounds might be beneficial in detecting flavor imbuing and/or other chemical compounds in an analyzed (wine) sample.

Some embodiments and examples herein may be discussed in the context of obtaining wave spectra of an analyzed sample using Fi-RT. It is noted that there are different types of infrared spectroscopy measurement techniques and embodiments herein might be implemented using other types of infrared spectroscopy, unless otherwise noted.

Different techniques might be used, for various practical purposes, to convert time series data into a visual image representation of the time series data. In some embodiments, the Markov transition fields (MTF) visualization technique might be used to convert or otherwise transform a set of time series data into a visual image representation (i.e., an image) of the set of time series data. Details of the MTF visualization technique are not the subject of the present disclosure and might include multiple process steps including, for example, discretizing the time series along the different values it can take, building a Markov transition matrix, computing transition probabilities, computing the Markov transition field, computing an aggregated MTF, extracting meaningful metrics, and mapping transition probabilities back to the initial signals. An important step of the MTF process is discretizing or binning an input signal (e.g., time series data) for the further process steps. In some embodiments herein, the spectra data for a (wine) sample might be converted to a set of discretized data as part of the MIT (or other) visualization process and further processed to generate an image representation of the full spectra data.

In some embodiments, the raw spectra data (e.g., the spectra data depicted in FIGS. 1A and 1B) might be processed, in essence, as time series data with the spectra data occurring over a particular wavelength occur over a time or over a distance.

FIGS. 2A-2C are illustrative example depictions of visual images derived from a conversion of the wave spectra graphs in FIGS. 1A-1C, respectively. The images in FIGS. 2A-2C include an image grid or matrix based on spectra time series. FIG. 2A is a visual image representation of the time series spectra of FIG. 1A, FIG. 2B is a visual image representation of the time series spectra of FIG. 1B, and FIG. 2C is an image representation of the combined time series spectra shown in FIG. 1C. Referring to FIG. 2C, some regions include pixels generated based on spectra strictly from either FIG. 1A or 1B. Those regions highlight differences between the two spectra 100 and 120. Some regions of FIG. 2C include a combination of pixels generated based on spectra from both FIGS. 1A and 1B, where the spectra overlay each other. For example, the image of FIG. 2C clearly illustrates there is significant overlay between these two time series as supported by the raw spectra data depicted in FIGS. 1A and 1B.

Figure 3:
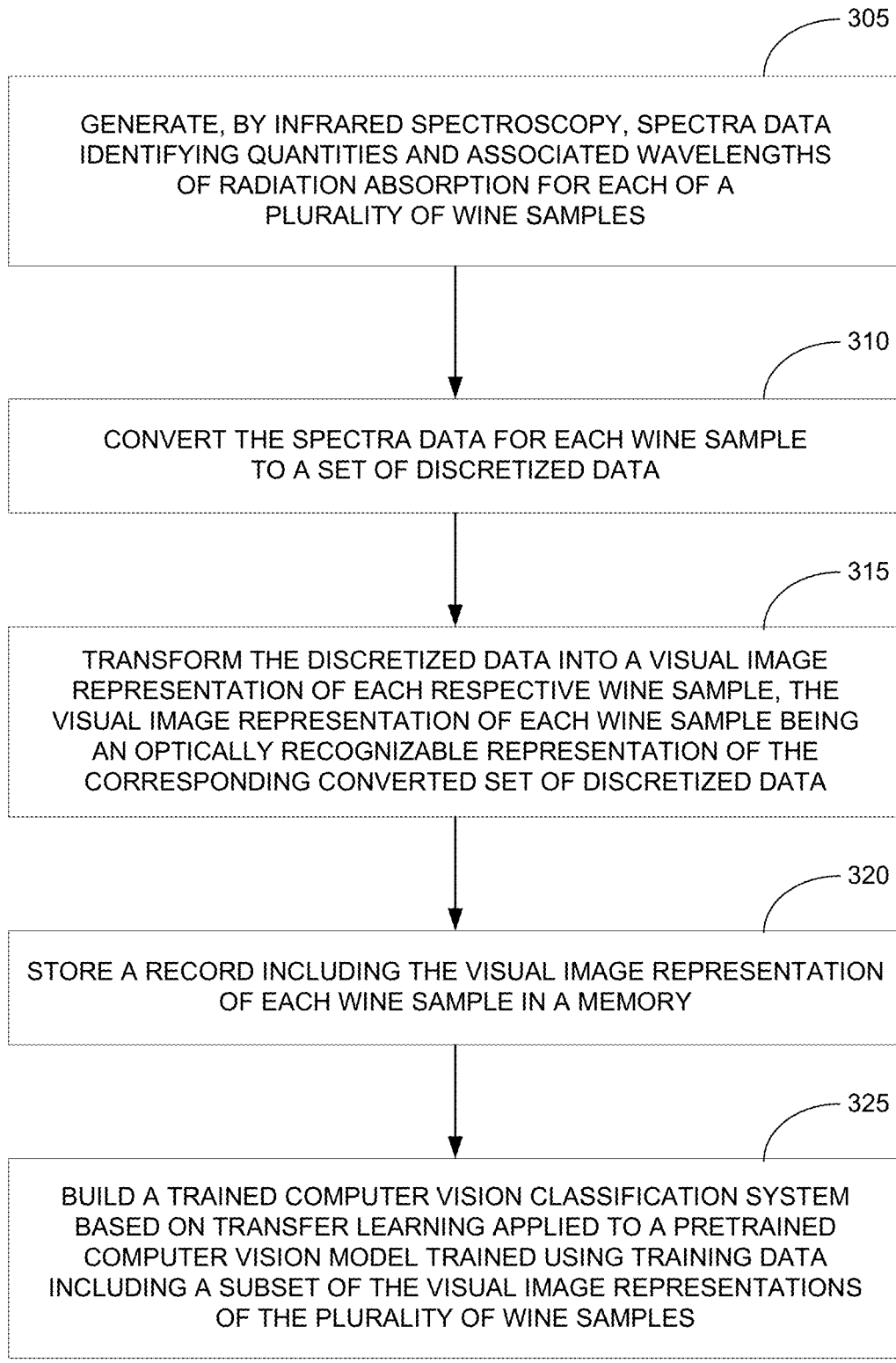
FIG. 3 is an illustrative flow diagram of a process, according to some embodiments.

FIG. 3 is an illustrative flow diagram for a process 300, according to some embodiments. In some aspects, process 300 relates to building a trained computer vision classification system, model, or system (in some aspects and instances herein, the terms system, model, or system might be used interchangeably with each other). At operation 305, spectra data is generated by infrared spectroscopy analysis of a sample (e.g., a consumable item such as, for example, a wine). The generated spectra data identifies quantities of chemical compound(s) and the associated wavelengths. FIGS. 1A and 1B are illustrative examples of the wave spectra graphs or diagrams that might be generated by Fi-RT spectroscopy in accordance with some embodiments of the present disclosure.

At operation 310, the spectra data generated in operation 305 is converted or otherwise processed to a set of discretized data. In some aspects the converting of the spectra data to discretized data facilitates and supports processing the spectra data as time series. Operation 315 further transforms the discretized data into a visual image representation of the full spectra of the analyzed (wine) sample. In some aspects, the visual image representation of the full spectra of the analyzed sample is an optically recognizable representation of the corresponding set of discretized data. As used herein, optically recognizable refers to an image that is machine readable by a computer vision system, including but not limited to a computer vision system including a machine learning model, algorithm, or network.

In some embodiments, operation 315 might include a MTF process. In some embodiments, operations 310 and 315 might comprise separate steps of a process (e.g., MTF), separate steps of different processes, or even be combined as one step of a common process (e.g., MTF or some other image visualization process or technique).

At operation 320, a record or other data structure including the visual image representation of the spectra for the analyzed sample (e.g., wine sample) may be stored in a memory device or system. The image of the spectra for the analyzed sample might be stored in the memory for further processing, including, for example, one or more of the other processes disclosed hereinbelow. The record might be stored in one or more of a local memory system (e.g., on-premise), in a cloud-based data storage system or service, or a hybrid cloud platform, where the memory might be distributed over one or more nodes or instances of a data storage system or service.

Process 300 continues at operation 325 that includes building or otherwise generating, a trained computer vision classification system. In some embodiments, the trained computer vision classification system may be built based on transfer learning applied to a pretrained computer vision model trained using training data including visual image representations of a plurality of wine samples. In some embodiments, the resulting trained vision classification system can, for example, recognize, distinguish, and disambiguate visual image representations of a new or other wine samples. In some embodiments, a trained computer vision classification system herein might be used to generate an output including a recommendation regarding a new (wine) sample based on, at least in part, visual image representations of one or more wine samples provided as input thereto. In some embodiments, the trained computer vision classification system or model might be built as disclosed in FIG. 4.

Figure 4:
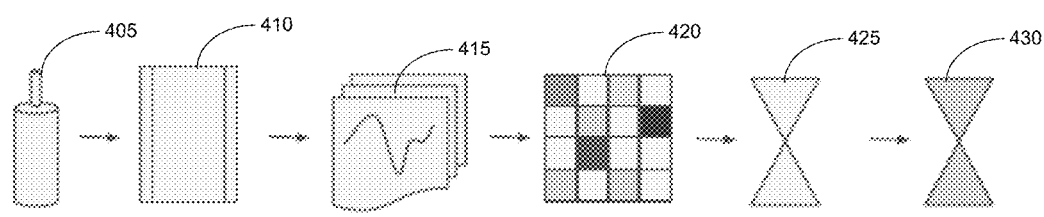
FIG. 4 is an illustrative depiction of an example processing pipeline for training a computer vision system, in accordance with some embodiments.

FIG. 4 is an illustrative depiction of an example processing pipeline 400 for building a trained a computer vision system, in accordance with some embodiments. Referring to FIG. 4, a beverage such as wine for example, may be analyzed by an infrared spectroscopy system (e.g., Fi-RT) 410 to produce spectra data 415 representative of each analyzed wine (or other) sample. The (raw) spectra data 415 for each sample is converted, transformed, or otherwise processed into a visual image representation 420 by a visualization process or algorithm (e.g., MTF). The visual image representation 420 of one or more wines 405 may be stored in a data storage memory system, database, or other data storage device, system, or database service instance. In some instances, storage and management of records or other data structures including data representations of the visual image representation 420 of one or more wines 405 might be provided by an on-demand cloud computing platform.

The output of the visualization process, that is the images 420 corresponding to the spectra data, are provided to a pre-trained computer vision model, system, or network 425. As used herein, pre-trained computer vision model 425 has been previously (i.e., pre-) trained to perform one or more visualization tasks related to computerized vision systems such as, for example, tasks or methods for object detection, image classification, visual relationship detection, image reconstruction, instance and semantic segmentation, etc. In some aspects, the pre-trained computer vision model 425 uses process(es) such as "transfer learning" to leverage knowledge of the pre-trained computer vision model 425 gained thereby learning to perform its designed tasks to further generate a trained computer vision classification model, system, or network 430.

In some aspects, the combination of the pre-trained computer vision model 425 and the application or use of transfer learning thereby enables and supports the generation of the trained computer vision classification model 430 based on even a limited number of images 420. For example, Applicant has realized a well performing trained computer vision classification model, system, or network 430 using about ten(10) images provided as input to a pre-trained computer vision model that further uses transfer learning to build the trained computer vision classification model.

The trained computer vision classification model, system, or network 430 is trained to visually detect and classify images consistent with the at least one specified classification associated with the images 420 provided as input(s) to the pre-trained computer vision model 425 to generate or build the trained computer vision classification model, system, or network 430.

FIG. 5 is an illustrative flow diagram for a process 500, according to some embodiments. In some aspects, process 500 relates to using a trained computer vision classification system to provide a recommendation regarding a wine (or other consumable food or beverage item). At operation 505, a user, retail outlet customer, wine or food club member, or other persons (individually and collectively referred to herein, at various points, as a "user") may acquire an image of one or more new wines of interest. In some embodiments, the new wine(s) might be acquired via an application, feature, system (e.g., camera), "app", or subsystem of a computing device operated by the user. In some instances, the computing device might be a portable or mobile computing device including, but not limited to a mobile phone, a tablet computer, a laptop computer, a smartwatch or other computing wearable device, where each of these devices is configured with a camera to acquire a photograph image of the one or more wines.

In some instances, the one or more new wines might comprise a wine included in an in-store display or shelf having the wines displayed for viewing and purchase. Accordingly, the wines may typically include a wine label that includes one or a combination of text and design images that convey the identity of the wine. That is, the text and images on the label distinguish the wine from other wines.

In some instances, the wine label affixed to or other parts of a container (e.g., bottle, box, carton, etc.) housing the wine might include other indicia representing an identity of the wine. In some embodiments, the other indicia might include encoded indicia such as, for example, a QR code, a barcode, a coded alphanumeric string, and other machine-readable labels or symbology. In some instances, the wine label affixed to or other parts of a container (e.g., bottle, box, carton, etc.) housing the wine might include a device to transmit a signal including information representing an identity of the wine. In some embodiments, the device to transmit the signal might include at least one of a radio-frequency identification (RFID) tag, a near-field communication (NFC) device, a Bluetooth communication device, and other short-range wireless technology communication protocol devices.

Referring to operation 505, the computing device operated by the user may function to identify the one or more wines in the acquired image. In some aspects, the computing device may use one or a combination of hardware and software components to identify at least one wine (or other consumable) in the acquired image. For example, the user might take a photograph of a store shelf supporting three different bottles of wine (e.g., wine A, B, and C). In another instance, the user might be in a restaurant and "scan" a menu including a textual listing of offered wines. In either of these scenarios, the user's computing device may be configured, including a combination of hardware (processors, memory, etc.) and software components thereof, to identify the wines in an image captured by the device's camera and associated hardware and software using, at least, optical character recognition (OCR) technologies. In some instances, at least a portion of the OCR processing to identify the wines in an image captured by the user's device may be processed by the user's computing device and at least another portion of the processing to identify the wines might be accomplished by a remote system (e.g., a cloud-based wine (or other) identification system or service, a backend system in communication with the user's computing (client) device (e.g., a server supporting the wine identification process of operation 505) via the Internet, etc.). Operation 505 may include OCR techniques and features to recognize and identify the wines in the acquired images. For example, the combination of text and images in an image of a bottle of wine in a store or the descriptive text name of a wine in a menu or wine list might be processed using OCR technologies to identify the wines in the captured image.

At operation 510, each of the wines identified in the acquired images may be correlated to a known visual image representation of the wines. For example, a system might have access to a library of hundreds or even thousands of visual image representations of known wines (e.g., previously obtained visual image representations of wines, such as illustrated by FIG. 4, visual image representations 420 (e.g., MTF images)), where each visual image representation of the known wines is a unique, optically recognizable representation of the respective wine (i.e., a wine "fingerprint").

Proceeding to operation 515, a trained computer vision classification system compatible with aspects herein may be executed, having inputs including (1) the visual image representation of each of the identified wines and (2) labeled visual image representations of at least one wine associated with a user flavor profile including at least one classification, to generate an output including a recommendation regarding the identified wines for the user. In some aspects, a recommendation might be provided in the generated output for each of the identified wines, wherein the output includes an indication of whether the identified wine corresponds to the at least one classification associated with the user flavor profile. For example, a flavor profile for a user might include one or more classifications of the user's flavor preferences (e.g., liked, not like, and neutral) regarding a plurality of wines. In one instance, a user's flavor profile may be based on the user providing, either directly or indirectly, an indication of their preference regarding ten different wines. For example, the user is a member of a wine club and provided their preference for eight different wines they purchased and purchased two other wines repeatedly. In this example, a system herein might generate a flavor profile for the user based on their direct feedback for the eight wines and infer the user liked the other two wines based on their repeated purchases thereof (e.g., three or more purchases of each of the two other wines). In some embodiments, customer-rated wines might be used by the trained computer vision network herein to understand what customers are drinking and preferring. In this manner, a flavor profile might be developed for user(s) through images. Furthermore, wine recommendations might be determined based on these flavor profiles.

A trained computer vision classification system herein might provide the output including a recommendation for each of the identified wines in a number of different formats, including, for example, a text output (e.g., a wine is "recommended" or "not recommended", with or without an accompanying degree of confidence (e.g., a percentage or a color indicative of a strength of the recommendation or non-recommendation); an icon or graphical indication (e.g., an emoji, a thumb up or thumb down icon, a green light or red light icon, etc.); an audible indication (e.g., an recommended chime or a not recommended buzzer, etc.); a dashboard in a graphical user interface including one or more of the foregoing or other formats of recommendations.

Figure 6:
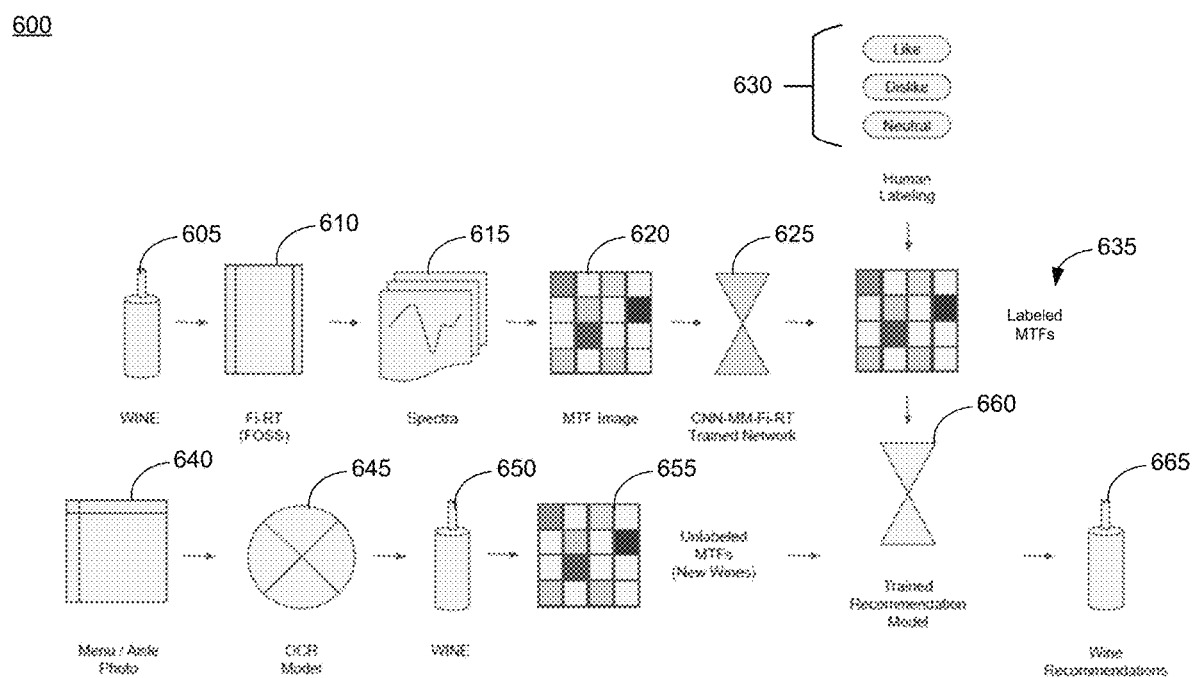
FIG. 6 is an illustrative depiction of an example processing pipeline for using a trained computer vision system, in accordance with some embodiments.

FIG. 6 is an illustrative depiction of an example processing pipeline 600 for using a trained computer vision system to generate wine shopping and dining recommendations, in accordance with some embodiments. Aspects of FIG. 6 relate to both the building of a trained computer vision system (e.g., based in some embodiments on machine learning, such as a deep learning convolutional neural network, CNN) and a use thereof in combination with other technologies as disclosed herein to generate wine shopping and dining recommendations tailored to a user. Some aspects of FIG. 6 are at least similar to aspects of FIGS. 3-5. As such, certain aspects common to FIGS. 3-5 and FIG. 6 might not be repeated in the discussion of FIG. 6.

Referring to FIG. 6, a plurality of wines 605 are analyzed by infrared spectroscopy (e.g., Fi-RT) 610 to obtain spectra data 615 that is representative of each analyzed wine (or other) sample. The wine spectra 615 data for each wine (or other) sample is converted, transformed, or otherwise processed into image a visual image representation by a visualization process or algorithm (e.g., MTF) 620 that is used to generate/build trained network 625. One or more of the images used to train network 625 are labeled based on a user's (e.g., a wine club member, a wine consumer or customer) preferences 630 (e.g., derived from their interaction with a wine club system and/or associated application or "app"). In some instances, the user's preferences relate to classifications of wines, including whether the user liked, disliked, or was neutral regarding a wine (other classification values may be used in some embodiments herein). Accordingly, visual image representations 635 are referred to herein as labeled visual image representations (e.g., MTFs).

Continuing with reference to FIG. 6, a user/customer/wine member (e.g., a user/customer/wine member that previously provided their wine preferences to system or processing pipeline 600) acquires an image or photograph including one or more wines by scanning an in-store aisle/display or menu/list of wines 640 using a camera and associated hardware and executable software on their mobile device (not shown). Using OCR technologies 645, that may be provided on-board the user's mobile device or by a remote system (e.g., a cloud-based service, system, or platform), features from the wine bottle label or menu/wine list of the acquired image 640 of the wines are identified at 650. Process 600 further includes correlating the identified wine(s) 650 to unlabeled visual image representations (e.g., MTF images) from a library (e.g., database or other stored record of MTF images) of analyzed wines to obtain an unlabeled visual image representation (e.g., MTF image) 655 of each new wine derived from the in-store aisle/display or menu/list of wines 640. The unlabeled visual image representations 655 corresponding to wine(s) 650 and the labeled visual image representation are provided as input(s) to trained recommendation engine 660. The trained recommendation engine 660 processes the input(s) thereto to output or otherwise generate a recommendation 665 (e.g., recommended (with associated confidence), not recommended (with alternative recommended wine), etc.). for the wine(s) 650. In this manner, the system or processing pipeline 600 might generate a recommendation for a new wine 650 based on the user/customer/wine member's flavor profile.

Figure 7:
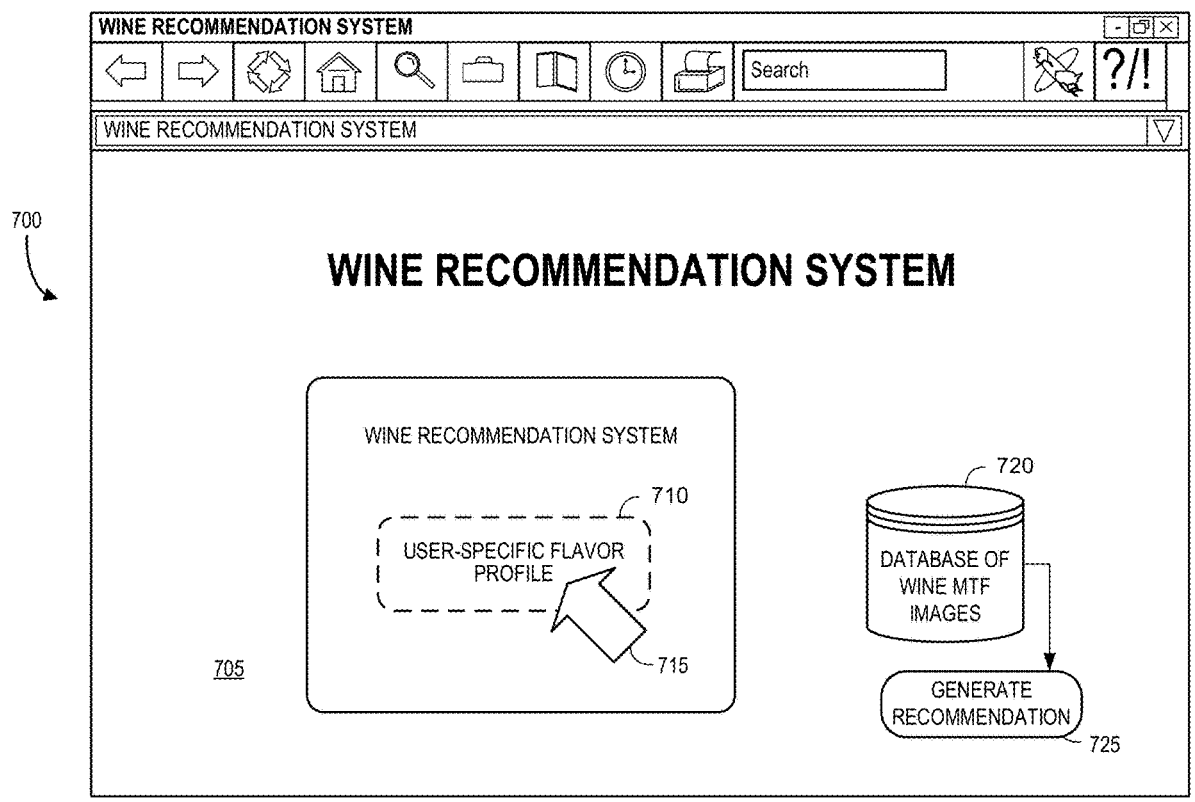
FIG. 7 is an outward facing user interface related to a system and process for a wine recommendation service, according to some embodiments.

FIG. 7 is an outward facing user interface related to a system and process for a wine recommendation system or service, according to some embodiments. FIG. 7 is a human-machine interface display 700 in accordance with some embodiments. The display 700 includes a graphical representation 705 or dashboard that might be used to interact with a wine recommendation system to provide inputs thereto and receive outputs therefrom. In particular, selection of an element (e.g., a user-specific flavor profile entry button 710 using tablet computer pointer 715) might result in the display of a popup window (not shown) that accepts a selection of a user's stored flavor profile or new entries of values for user preferences from a user (i.e., the user's personal preferences regarding wines). Display 700 also includes a representation of a database of wine MTF images. Display 700 includes a user selectable "Generate Recommendation" icon 725 to request a data-driven recommendation for a "new" wine (e.g., acquired by the user using a camera of the user's mobile device and OCR techniques, per some example embodiments herein) for the user that is determined based on the user's specific flavor profile.

Figure 8:
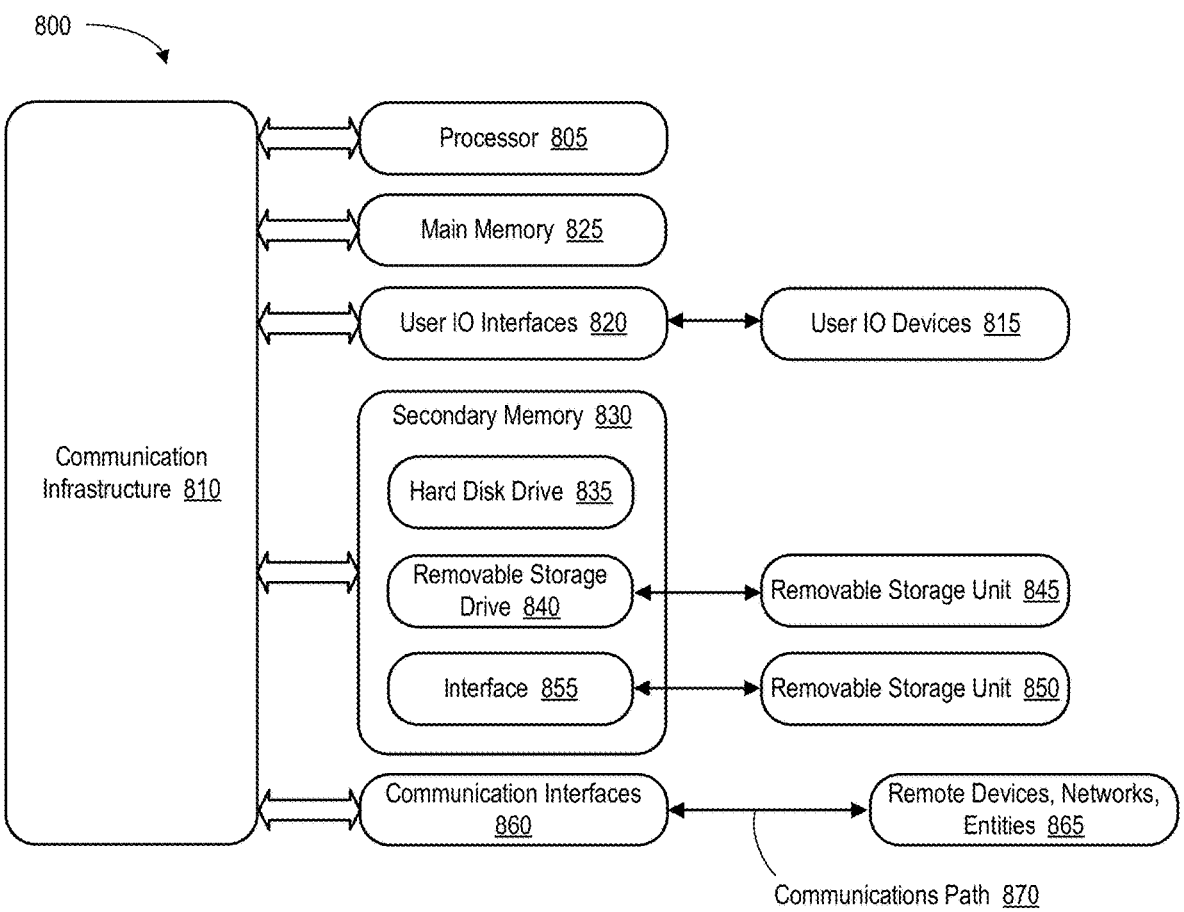
FIG. 8 is illustrative example of a computing system for use in some example embodiments disclosed herein.

Various embodiments can be implemented, for example, using one or more well-known computer systems, such as computer system 800 shown in FIG. 8. The computer system 800 can be any well-known computer capable of performing the functions described herein. Computer system 800 includes one or more processors (also called CPUs), such as a processor 805. Processor 805 is connected to a communication infrastructure or bus 810.

One or more processors 805 may each be a Graphics Processing Unit ("GPU"). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 800 also includes user input/output device(s) 815, such as monitors, keyboards, pointing devices, etc., that communicate with communication infrastructure xx010 through user input/output interface(s) 820.

Computer system 800 also includes a main or primary memory 825, such as Random-Access Memory ("RAM"). Main memory 825 may include one or more levels of cache. Main memory 825 has stored therein control logic (i.e., computer software) and/or data.

Computer system 800 may also include one or more secondary storage devices or memory 830. Secondary memory 830 may include, for example, a hard disk drive 835 and/or a removable storage device or drive 840. Removable storage drive 840 may be a floppy disk drive, a magnetic tape drive, a compact disk drive, an optical storage device, tape backup device, and/or any other storage device/drive.

Removable storage drive 840 may interact with a removable storage unit 845. Removable storage unit 845 includes a computer usable or readable storage device having stored thereon computer software (control logic) and/or data. Removable storage unit 845 may be a floppy disk, magnetic tape, compact disk, DVD, optical storage disk, and/any other computer data storage device. Removable storage drive 840 reads from and/or writes to removable storage unit 845 in a well-known manner.

According to an exemplary embodiment, secondary memory 830 may include other means, instrumentalities or other approaches for allowing computer programs and/or other instructions and/or data to be accessed by computer system 800. Such means, instrumentalities or other approaches may include, for example, a removable storage unit 850 and an interface 855. Examples of the removable storage unit 850 and the interface 855 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 800 may further include a communication or network interface 860. Communication interface 860 enables computer system 800 to communicate and interact with any combination of remote devices, remote networks, remote entities, etc. (individually and collectively referenced by reference number 865). For example, communication interface 860 may allow computer system 800 to communicate with remote devices 865 over communications path 870, which may be wired and/or wireless, and which may include any combination of LANs, WANs, the Internet, etc. Control logic and/or data may be transmitted to and from computer system 800 via communication path 870.

In an embodiment, a tangible apparatus or article of manufacture comprising a tangible computer useable or readable medium having control logic (software) stored thereon is also referred to herein as a computer program product or program storage device. This includes, but is not limited to, computer system 800, main memory 825, secondary memory 830, and removable storage units 845 and 850, as well as tangible articles of manufacture embodying any combination of the foregoing. Such control logic, when executed by one or more data processing devices (such as computer system 800), causes such data processing devices to operate as described herein.

Based on the teachings contained in this disclosure, it will be apparent to persons skilled in the relevant art(s) how to make and use embodiments of the invention using data processing devices, computer systems and/or computer architectures other than that shown in FIG. 8. In particular, embodiments may operate with software, hardware, and/or operating system implementations other than those described herein.

Although specific hardware and data configurations have been described herein, note that any number of other configurations may be provided in accordance with some embodiments of the present invention (e.g., some of the information associated with the databases and storage elements described herein may be combined or stored in external systems). Moreover, although some embodiments are focused on particular types of applications and services, any of the embodiments described herein could be applied to other types of applications and services. In addition, the displays shown herein are provided only as examples, and any other type of user interface could be implemented.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A computer-implemented method, the method comprising:
    generating, by infrared spectroscopy, spectra data identifying quantities and associated wavelengths of radiation absorption for each of a plurality of wine samples as determined by the infrared spectroscopy;
    converting the spectra data for each wine sample to a set of discretized data;
    transforming the discretized data into a visual image representation of each respective wine sample, the visual image representation of each wine being an optically recognizable representation of the corresponding converted set of discretized data;
    storing a record including the visual image representation of each wine sample in a memory;
    building the trained computer vision classification system based on transfer learning applied to a pretrained computer vision model trained using training data including a subset of a plurality of visual image representations of the plurality of wine samples;
    acquiring an image including an indication of at least one wine;
    identifying, by optical character recognition, the at least one wine in the acquired image;
    correlating each of the identified at least one wines to a visual image representation of each wine; and
    executing the trained computer vision classification system using (1) the visual image representation of each of the identified wines and (2) labeled visual image representations of at least one wine associated with a user flavor profile including at least one classification as inputs to generate an output including, for each of the identified wines, an indication of whether the identified wine corresponds to the at least one classification associated with the user flavor profile.

2. The method of claim 1, wherein the visual image representation of each wine correlated to each of the identified at least one wines is obtained from the stored record.

3. The method of claim 1, wherein the infrared spectroscopy includes Fourier transform infrared spectroscopy.

4. The method of claim 1, wherein the indication of the at least one wine is at least one of a label affixed to a container of wine, a textual representation of a wine, encoded indicia identifying a wine; and an encoded signal including an identifier of a wine.

5. The method of claim 1, wherein the encoded indicia are at least one of QR code, a bar code, and other machine-readable optical label.

6. The method of claim 1, wherein the encoded signal is generated by at least one of a radio-frequency identification (RFID) tag, a near-field communication device, a bluetooth communication device, and other short-range wireless technology communication protocol device.

7. A system comprising:
    a processor;
    a storage device; and
    a memory in communication with the processor, the memory storing program instructions, the processor operative with the program instructions to perform the operations of:
        generating, by infrared spectroscopy, spectra data identifying quantities and associated wavelengths of radiation absorption for each of a plurality of wine samples as determined by the infrared spectroscopy;
        converting the spectra data for each wine sample to a set of discretized data;
        transforming the discretized data into a visual image representation of each respective wine sample, the visual image representation of each wine being an optically recognizable representation of the corresponding converted set of discretized data;
        storing a record including the visual image representation of each wine sample in a memory;
        building the trained computer vision classification system based on transfer learning applied to a pretrained computer vision model trained using training data including a subset of a plurality of visual image representations of the plurality of wine samples;
        acquiring an image including an indication of at least one wine;
        identifying, by optical character recognition, the at least one wine in the acquired image;
        correlating each of the identified at least one wines to a visual image representation of each wine; and
        executing the trained computer vision classification system using (1) the visual image representation of each of the identified wines and (2) labeled visual image representations of at least one wine associated with a user flavor profile including at least one classification as inputs to generate an output including, for each of the identified wines, an indication of whether the identified wine corresponds to the at least one classification associated with the user flavor profile.

8. The system of claim 7, wherein the visual image representation of each wine correlated to each of the identified at least one wines is obtained from the stored record.

9. The system of claim 7, wherein the infrared spectroscopy includes Fourier transform infrared spectroscopy.

10. The system of claim 7, wherein the indication of the at least one wine is at least one of a label affixed to a container of wine, a textual representation of a wine, encoded indicia identifying a wine; and an encoded signal including an identifier of a wine.

11. The system of claim 7, wherein the encoded indicia are at least one of QR code, a bar code, and other machine-readable optical label.

12. The system of claim 7, wherein the encoded signal is generated by at least one of a radio-frequency identification (RFID) tag, a near-field communication device, a bluetooth communication device, and other short-range wireless technology communication protocol device.

13. A non-transient, computer-readable medium storing instructions to be executed by a processor to perform a method, the method comprising:
    generating, by infrared spectroscopy, spectra data identifying quantities and associated wavelengths of radiation absorption for each of a plurality of wine samples as determined by the infrared spectroscopy;
    converting the spectra data for each wine sample to a set of discretized data;
    transforming the discretized data into a visual image representation of each respective wine sample, the visual image representation of each wine being an optically recognizable representation of the corresponding converted set of discretized data;

storing a record including the visual image representation of each wine sample in a memory;

building the trained computer vision classification system based on transfer learning applied to a pretrained computer vision model trained using training data including a subset of a plurality of visual image representations of the plurality of wine samples;

acquiring an image including an indication of at least one wine;

identifying, by optical character recognition, the at least one wine in the acquired image;

correlating each of the identified at least one wines to a visual image representation of each wine; and executing the trained computer vision classification system using (1) the visual image representation of each of the identified wines and (2) labeled visual image representations of at least one wine associated with a user flavor profile including at least one classification as inputs to generate an output including, for each of the identified wines, an indication of whether the identified wine corresponds to the at least one classification associated with the user flavor profile.

14. The medium of claim 13, wherein the visual image representation of each wine correlated to each of the identified at least one wines is obtained from the stored record.

15. The medium of claim 13, wherein the indication of the at least one wine is at least one of a label affixed to a container of wine, a textual representation of a wine, encoded indicia identifying a wine; and an encoded signal including an identifier of a wine.

16. The medium of claim 13, wherein the encoded indicia are at least one of QR code, a bar code, and other machine-readable optical label.

17. The medium of claim 13, wherein the encoded signal is generated by at least one of a radio-frequency identification (RFID) tag, a near-field communication device, a bluetooth communication device, and other short-range wireless technology communication protocol device.

* * * * *